(12) United States Patent
Oldham et al.

(10) Patent No.: US 7,491,924 B2
(45) Date of Patent: *Feb. 17, 2009

(54) COMBINATION READER

(75) Inventors: Mark F. Oldham, Los Gatos, CA (US); Howard G. King, Berkeley, CA (US); Douwe D. Haga, Redwood City, CA (US); Tracy L. Ferea, Mountain View, CA (US)

(73) Assignee: Applera Corporation, Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/781,515

(22) Filed: Jul. 23, 2007

(65) Prior Publication Data

US 2007/0263209 A1 Nov. 15, 2007

Related U.S. Application Data

(60) Continuation of application No. 11/580,100, filed on Oct. 12, 2006, now abandoned, which is a division of application No. 11/188,243, filed on Jul. 22, 2005, now Pat. No. 7,135,667, which is a division of application No. 10/384,995, filed on Mar. 10, 2003, now Pat. No. 6,970,240.

(51) Int. Cl.
- *G01N 21/86* (2006.01)
- *G01T 1/20* (2006.01)
- *G01V 8/00* (2006.01)
- *H01L 27/00* (2006.01)

(52) U.S. Cl. ............ 250/208.1; 250/559.4; 250/361 R; 356/417

(58) Field of Classification Search ......... 250/234–236, 250/339.11–339.12, 361 R, 370.08, 458.1, 250/461.1, 461.2, 208.1, 559.4, 583–586; 356/317–318, 417; 435/5, 6, 34, 40.5
See application file for complete search history.

(56) References Cited

U.S. PATENT DOCUMENTS

| 4,554,839 A | 11/1985 | Hewett et al. |
| 4,952,518 A | 8/1990 | Johnson et al. |
| 5,274,240 A | 12/1993 | Mathies et al. |

(Continued)

FOREIGN PATENT DOCUMENTS

EP 0452905 10/1991

(Continued)

OTHER PUBLICATIONS

International Search Report, PCT/US2004/007103, Int'l Filing Date: Mar. 9, 2004 (6 sheets).

*Primary Examiner*—John R Lee
(74) *Attorney, Agent, or Firm*—Harness, Dickey & Pierce, P.L.C.

(57) ABSTRACT

An apparatus for imaging an array of a plurality of features associated with a sample tile. The apparatus includes a stage that supports the sample tile in an illumination region, and an illumination source having a plurality of LEDs adapted to emit light. At least a portion of the light illuminates the illumination region. Additionally, the apparatus includes an image collecting device adapted to selectively collect images of a signal.

21 Claims, 5 Drawing Sheets

U.S. PATENT DOCUMENTS

| | | | |
|---|---|---|---|
| 5,281,804 A | 1/1994 | Shirasaki | |
| 5,283,179 A | 2/1994 | Wood | |
| 5,578,832 A | 11/1996 | Trulson et al. | |
| 5,625,077 A | 4/1997 | Bronstein | |
| 5,631,743 A | 5/1997 | Inoue et al. | |
| 5,641,641 A | 6/1997 | Wood | |
| 5,652,345 A | 7/1997 | Schaap et al. | |
| 5,679,803 A | 10/1997 | Bronstein et al. | |
| 5,741,463 A | 4/1998 | Sanadi | |
| 5,783,381 A | 7/1998 | Bronstein et al. | |
| 5,834,758 A | 11/1998 | Trulson et al. | |
| 5,837,546 A | 11/1998 | Allen et al. | |
| 5,925,525 A | 7/1999 | Fodor et al. | |
| 5,936,324 A | 8/1999 | Montagu | |
| 5,954,416 A | 9/1999 | Peterson | |
| 5,981,956 A | 11/1999 | Stern | |
| 5,985,214 A | 11/1999 | Stylli et al. | |
| 5,998,768 A | 12/1999 | Hunter et al. | |
| 5,999,209 A | 12/1999 | Hunter et al. | |
| 6,001,309 A | 12/1999 | Gamble et al. | |
| 6,005,664 A | 12/1999 | Korenberg et al. | |
| 6,022,964 A | 2/2000 | Bronstein et al. | |
| 6,025,601 A | 2/2000 | Trulson et al. | |
| 6,040,138 A | 3/2000 | Lockhart et al. | |
| 6,040,193 A | 3/2000 | Winkler et al. | |
| 6,082,797 A | 7/2000 | Antonette | |
| 6,088,100 A | 7/2000 | Brenan et al. | |
| 6,099,230 A | 8/2000 | Hitch | |
| 6,124,478 A | 9/2000 | Bronstein et al. | |
| 6,133,459 A | 10/2000 | Schaap et al. | |
| 6,141,096 A | 10/2000 | Stern et al. | |
| 6,160,618 A | 12/2000 | Garner | |
| 6,197,572 B1 | 3/2001 | Schneebeli et al. | |
| 6,215,894 B1 | 4/2001 | Zeleny et al. | |
| 6,220,451 B1 | 4/2001 | Hoffmann et al. | |
| 6,228,659 B1 | 5/2001 | Kowallis et al. | |
| 6,252,236 B1 | 6/2001 | Trulson et al. | |
| 6,253,807 B1 | 7/2001 | Jones et al. | |
| 6,271,042 B1 | 8/2001 | Watson, Jr. et al. | |
| 6,323,035 B1 | 11/2001 | Kedar et al. | |
| 6,325,114 B1 | 12/2001 | Bevirt et al. | |
| 6,329,661 B1 | 12/2001 | Perov et al. | |
| 6,349,160 B2 | 2/2002 | Tsien et al. | |
| 6,353,475 B1 | 3/2002 | Jensen et al. | |
| 6,372,185 B1 | 4/2002 | Shumate et al. | |
| 6,387,675 B1 | 5/2002 | Wood et al. | |
| 6,403,957 B1 | 6/2002 | Fodor et al. | |
| 6,407,858 B1 | 6/2002 | Montagu | |
| 6,413,722 B1 | 7/2002 | Arnold et al. | |
| 6,416,719 B1 | 7/2002 | Fawcett et al. | |
| 6,420,180 B1 | 7/2002 | Bass | |
| 6,426,215 B1 | 7/2002 | Sandell | |
| 6,447,723 B1 | 9/2002 | Schermer et al. | |
| 6,448,089 B1 | 9/2002 | Vuong | |
| 6,468,800 B1 | 10/2002 | Stylli et al. | |
| 6,471,916 B1 | 10/2002 | Noblett | |
| 6,479,301 B1 | 11/2002 | Balch et al. | |
| 6,496,309 B1 | 12/2002 | Bliton et al. | |
| 6,504,607 B2 | 1/2003 | Jensen et al. | |
| 6,506,611 B2 | 1/2003 | Bienert et al. | |
| 6,545,264 B1 | 4/2003 | Stern | |
| 6,558,623 B1 | 5/2003 | Ganz et al. | |
| 6,583,424 B2 | 6/2003 | Staton et al. | |
| 6,586,257 B1 | 7/2003 | Vuong | |
| 6,597,000 B2 | 7/2003 | Stern | |
| 6,599,693 B1 | 7/2003 | Webb | |
| 6,608,671 B2 | 8/2003 | Tsien et al. | |
| 6,638,483 B2 | 10/2003 | Vuong | |
| 6,643,076 B2 | 11/2003 | Montagu | |
| 6,646,243 B2 | 11/2003 | Pirrung et al. | |
| 6,660,233 B1 | 12/2003 | Coassin et al. | |
| 6,672,344 B1 | 1/2004 | Stokes et al. | |
| 6,678,577 B1 | 1/2004 | Stylli et al. | |
| 6,685,884 B2 | 2/2004 | Stylli et al. | |
| 6,720,149 B1 | 4/2004 | Rava et al. | |
| 6,741,344 B1 | 5/2004 | Stern et al. | |
| 6,752,182 B2 | 6/2004 | Atkinson et al. | |
| 6,794,658 B2 | 9/2004 | MacAulay et al. | |
| 6,814,933 B2 | 11/2004 | Vuong | |
| 6,825,927 B2 | 11/2004 | Goldman et al. | |
| 6,852,986 B1 | 2/2005 | Lee et al. | |
| 6,970,240 B2 * | 11/2005 | Oldham et al. | 356/317 |
| 7,081,954 B2 * | 7/2006 | Sandstrom | 356/317 |
| 7,135,667 B2 * | 11/2006 | Oldham et al. | 250/208.1 |
| 2002/0098593 A1 | 7/2002 | Nelson et al. | |
| 2002/0110828 A1 | 8/2002 | Ferea et al. | |
| 2002/0119077 A1 | 8/2002 | Shumate et al. | |
| 2002/0173048 A1 | 11/2002 | Nakazawa et al. | |
| 2002/0176803 A1 | 11/2002 | Hamel et al. | |
| 2002/0179849 A1 | 12/2002 | Maher et al. | |
| 2002/0182117 A1 | 12/2002 | Coassin et al. | |
| 2002/0192716 A1 | 12/2002 | Schellenberger et al. | |
| 2003/0008286 A1 | 1/2003 | Zoou et al. | |
| 2003/0017085 A1 | 1/2003 | Kercso et al. | |
| 2003/0032198 A1 | 2/2003 | Lugmair et al. | |
| 2003/0038248 A1 | 2/2003 | Maher et al. | |
| 2003/0095254 A1 | 5/2003 | Tanaami | |
| 2003/0096427 A1 | 5/2003 | Hall | |
| 2003/0112432 A1 | 6/2003 | Yguerabide et al. | |
| 2003/0124735 A1 | 7/2003 | Nanthakumar et al. | |
| 2003/0136921 A1 | 7/2003 | Reel | |
| 2003/0138829 A1 | 7/2003 | Unger et al. | |
| 2003/0161761 A1 | 8/2003 | Williams et al. | |
| 2003/0170613 A1 | 9/2003 | Straus | |
| 2003/0198575 A1 | 10/2003 | Noda et al. | |
| 2003/0202637 A1 | 10/2003 | Yang | |
| 2003/0205681 A1 | 11/2003 | Modlin | |
| 2003/0215360 A1 | 11/2003 | Ruddock | |
| 2003/0215956 A1 | 11/2003 | Reed | |
| 2004/0018635 A1 | 1/2004 | Peck et al. | |
| 2004/0029109 A1 | 2/2004 | Lai | |
| 2004/0057870 A1 | 3/2004 | Isaksson et al. | |
| 2004/0061071 A1 | 4/2004 | Dorsel | |
| 2004/0062686 A1 | 4/2004 | Ganz et al. | |
| 2004/0096984 A1 | 5/2004 | Elverd et al. | |
| 2004/0110275 A1 | 6/2004 | Sandell | |
| 2004/0126283 A1 | 7/2004 | Backes et al. | |
| 2004/0136868 A1 | 7/2004 | Bevirt et al. | |
| 2004/0202577 A1 | 10/2004 | McNeil et al. | |
| 2004/0203047 A1 | 10/2004 | Caren et al. | |
| 2004/0203164 A1 | 10/2004 | Cizdziel et al. | |

FOREIGN PATENT DOCUMENTS

| | | |
|---|---|---|
| WO | WO-94/27719 | 12/1994 |
| WO | WO-95/11262 | 4/1995 |
| WO | WO-96/33010 | 10/1996 |
| WO | WO-00/59671 | 10/2000 |
| WO | WO-01/35079 | 5/2001 |
| WO | WO-01/63247 | 8/2001 |
| WO | WO-02/08754 | 1/2002 |
| WO | WO-03/010524 | 3/2003 |

* cited by examiner

COMBINATION READER

CROSS-REFERENCE TO RELATED APPLICATIONS

This application is a continuation of U.S. patent application Ser. No. 11/580,100 filed Oct. 12, 2006 now abandoned, which is a divisional of U.S. patent application Ser. No. 11/188,243 filed Jul. 22, 2005, now U.S. Pat. No. 7,135,667 which is a divisional of U.S. patent application Ser. No. 10/384,995 filed Mar. 10, 2003, now U.S. Pat. No. 6,970,240. The disclosures of the above applications are incorporated herein by reference.

FIELD

The invention relates generally to imaging biomolecular or synthetic arrays.

BACKGROUND

Substrate-bound biomolecular or synthetic arrays, such as oligonucleotide arrays, also known as micro arrays, enable the testing of the hybridization of different sequences in a sample to many different probes. These arrays can be composed of hundreds of thousands of probes deposited or synthesized within specific regions, defined as features, on a substrate.

To analyze such arrays, the sample is labeled with one or more detectable markers, such as fluorescent or chemiluminescent markers, that hybridize with the probes at each feature on the substrate. The markers emit luminous signals, for example a fluorescent signal or a chemiluminescent signal, that are imaged and the images are analyzed.

SUMMARY

In various configurations, an apparatus is provided for imaging an array of a plurality of features associated with a sample tile. The apparatus includes a stage that supports the sample tile in an illumination region, and an illumination source having a plurality of LEDs adapted to emit light. At least a portion of the light illuminates the illumination region. Additionally, the apparatus includes an image collecting device adapted to selectively collect images of a signal.

BRIEF DESCRIPTION OF THE DRAWINGS

The present invention will become more fully understood from the detailed description and accompanying drawings, wherein.

DETAILED DESCRIPTION

The following description is merely exemplary in nature and in no way is intended to limit the invention, its application, or use.

Figure 1:
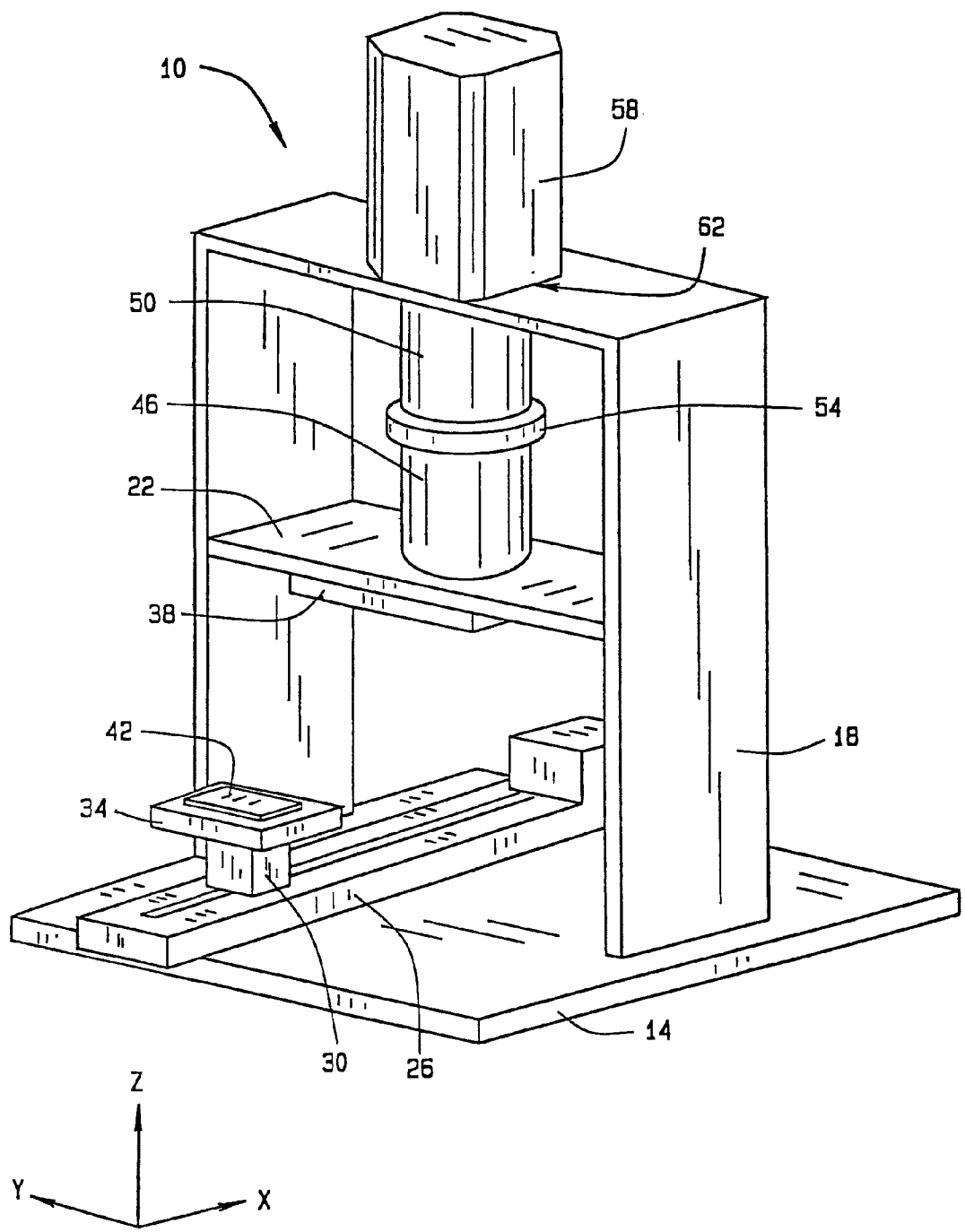
FIG. 1 is a perspective view of an imaging apparatus for collecting images of fluorescent and chemiluminescent hybridized markers in a biomolecular or synthetic sample.

FIG. 1 is a perspective view representative of various configurations of an imaging apparatus 10 for collecting images of fluorescent and chemiluminescent hybridized markers in a biomolecular or synthetic sample. The imaging apparatus 10 includes a base 14, a frame 18 connected to the base 14, and a mid-support 22 coupled to the frame 18. Additionally, the imaging apparatus 10 includes a transport 26 and an elevator 30 that are controlled by a controller (not shown) to orient a stage 34 under an illuminator 38 that illuminates a sample tile 42 positioned on the stage 34. The sample tile 42 is a support, such as glass, ceramic, or plastic, to which at least one feature of a sample (not shown) is associated, i.e. placed, synthesized, or attached. The feature can be, for example, any feature of the sample where a fluorescent and/or chemiluminescent marker has hybridized with a probe attached to the sample tile 42. For example, the feature can be a co-spotted oligonucleotides labeled with one fluorescent marker and one chemiluminescent marker.

In various configurations, the sample tile 42 includes an array of associated features having, for example, hundreds or thousands of features. In some configurations, the sample tile 42 includes a microarray having a larger plurality of associated features, for example, tens of thousands or hundreds of thousands of features. For the sake of convenience and clarity, exemplary configurations will be described below referencing an array of features, but it will be understood that the array could include as few as one feature, or the array could include as many as hundreds of thousands of features, or more.

In various configurations the array of features is a nucleic acid microarray. Such microarrays are becoming an increasingly important tool in bioanalysis and related fields. Nucleic acid microarrays have been developed and find use in a variety of applications, such as gene sequencing, monitoring gene expression, gene mapping, bacterial identification, drug discovery, and combinatorial chemistry. One area in particular in which microarrays find use is in gene expression analysis. Current methods of manufacturing nucleic acid microarrays, and methods of their use as diagnostic assays have been described in U.S. Pat. Nos. 6,413,722, 6,215,894, 6,040,193, 6,040,138, and 6,387,675.

Furthermore, the imaging apparatus 10 in various configurations includes a first lens 46, a second lens 50, a first filter 54, and an image collecting device 58. The first and second lenses 46 and 50 can be any lenses suitable for optical imaging performance, for example medium format photographic lenses. In some configurations not illustrated, a single lens is used for optical imaging performance. In various configurations, the first filter 54 is a longpass filter adapted to pass light having longer wavelengths, for example light having a wavelength greater than about 670 nm., or the first filter 54 is a bandpass filter adapted to pass light having wavelengths included in a certain range of wavelengths, for example light having wavelengths that are between about 670 nm and about 700 nm.

The image collecting device 58 and the second lens 50 are positioned in relation to each other such that a primary imaging surface 62 of image collection device 58 is at the focal plane of the second lens 50. The controller utilizes the transport 26 and the elevator 30 to position the stage 34 such that the tile 42 is at a focal plane of the first lens 46. The transport 26 moves the stage 34 along an x-axis, while the elevator 30 moves the stage 34 along a z-axis. Both the transport 26 and the elevator 30 are controlled by software via the controller, which interfaces with a computer workstation (not shown). Through the workstation, a user enters a command, e.g. "load sample", which is communicated to the controller. The controller interprets the command and utilizes at least one motor (not shown) to move the stage along the x-axis and z-axis to the commanded position. In various configurations the workstation is separate from the imaging apparatus 10. In other various configurations the imaging apparatus 10 includes the workstation. In other various configurations, the imaging apparatus 10 includes various computer workstation components, such as memory and a processor, while other computer workstation components, such as a graphical user interface, are separate from the imaging apparatus 10.

In various configurations, the controller and the transport 26 move the stage 34 to pre-set x-axis positions when loading the tile 42 and imaging the features of the array. For example, in some configurations, the controller is configured to instruct the transport 26 to move the stage 34 to a "loading the sample" position, an "imaging position #1" under illuminator 38, and an "imaging position #2" under the illuminator 38. The elevator 34 is controlled by the controller to position the stage 34 at the focal plane of the first lens 46. The elevator 30 moves the stage 34 along a z-axis, while the first and second lenses 46 and 50 remain stationary to achieve an optimum focus of the array for the image collecting device 58. An algorithm processes image data collected by image collecting device 58 to determine the position for optimum focus of the array. Therefore, an image of the array is auto-focused for the image collecting device 58 without adjusting the first and second lenses 46 and 50.

For example, image collecting device 58 collects imaging data and communicates the data to the workstation where the algorithm determines the clarity of the image. That is, the algorithm analyzes the contrast of the image. If the image does not have a desired contrast, the algorithm instructs the controller to adjust the position of the stage along the z-axis. Then another image is collected and the data is communicated to the workstation where the algorithm again analyzes the contrast. This process is repeated until the contrast is maximized, i.e. an optimum focus is achieved. In various configurations, the fluorescent signals emitted by each fluorescent marker are used by the algorithm to auto-focus the array. In some configurations, the elevator 30 is adapted to rotate the stage 34 in the x-y plane, and the transport 26 is adapted to move the stage 34 along the y-axis.

When the stage 34 is positioned under the illuminator 38, at the focal plane of the first lens 46, the image collecting device 58 collects at least one image of the array of features associated with the tile 42. For example, if the sample tile 42 is in an environment illuminated using the illuminator 38, the image collecting device 58 collects illumination data relating to the intensity of light emitted by the fluorescent marker in each feature. Or, for example, if the sample tile 42 is an environment absent light that will interfere with the chemiluminescent signals, the image collecting device 58 collects illumination data relating to the intensity of light emitted by the chemiluminescent markers in each feature. The image collecting device 58 can be any device suitable for collecting image data emitted from the array of features. For example, in some configurations, image collecting device 58 is configured to be a CMOS detector array. In some configurations the image collecting device 58 comprises a charge-coupled device (CCD).

Figure 2:
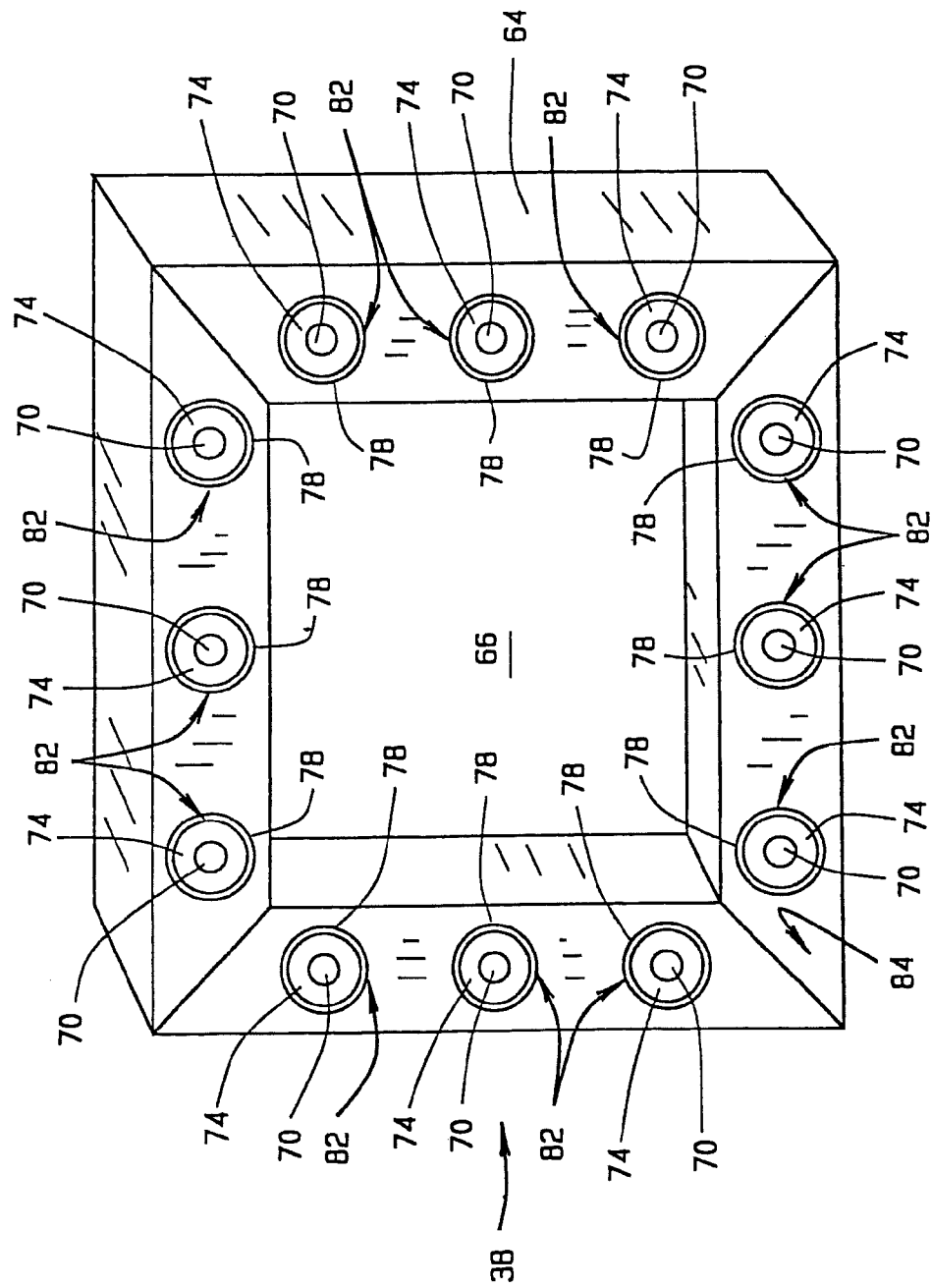
FIG. 2 is a perspective view of an illuminator shown in FIG. 1.

FIG. 2 is a perspective view representative of various configurations of the illuminator 38 (shown in FIG. 1). The illuminator 38 comprises a light source configured to excite the fluorescent marker in each feature by flooding the entire tile 42 (shown in FIG. 1) with light. That is, the illuminator 38 distributes light over the entire tile 42, exciting the fluorescent markers in all features associated with the tile 42 at the same time. Additionally, the illuminator 38 substantially evenly distributes light over the tile 42, such that approximately the same amount of light is distributed over the entire tile 42. The evenly distributed flood illumination provides approximately 360° of light to each feature, thereby allowing more accurate evaluation of the feature by exciting a greater percentage of the fluorescence of each feature, possibly the entire fluorescence of each feature. More specifically, artifacts, i.e. irregularities, in the top surface are less likely to block the excitation light from reaching all areas of the top surface of each feature. Furthermore, flooding the tile and associated array with light from approximately 360° allows a shape and a size of each feature in the array to be easily determined.

In various configurations, the illuminator 38 includes an opening 66 configured to allow images, i.e. fluorescent and/or chemiluminescent light signals, emitted from each feature to pass through the opening 66. The signals are then re-imaged by the first and second lenses 46, 50 (shown in FIG. 1), filtered by the first filter 54 (shown in FIG. 1), and collected by the image collecting device 58 (shown in FIG. 1). Although the illuminator 38 and opening 66 are shown in FIG. 2 as having a rectangular shape, the illuminator 38 and opening 66, in various configurations, can have any geometric shape suitable to flood illuminate the tile 42. In various configurations, for example, the shape of the illuminator 38 matches the shape of the tile 42. For example, in configurations in which the tile 42 is rectangular, the illuminator 38 and opening 66 are also rectangular. In configurations in which the tile 42 is round, the illuminator 38 and opening 66 are likewise round.

Additionally, in various configurations, illuminator 38 can have a continuous ring form, comprising a single continuous body 64 that provides the opening 66, as shown in FIG. 2. Additionally, in various configurations illuminator 38 can have a discontinuous ring form having a plurality of disconnected sections (not shown) that provides the opening 66. For example, illuminator 38 could have discontinuous ring form comprising two disconnected essentially semi-circular sections, or four disconnected straight sections that form a rectangular ring disconnected at the corners.

In various configurations, the illuminator 38 includes a plurality of LEDs 70, wherein each LED 70 is associated with one of a plurality of second filters 74 and one of a plurality of diffusers 78. For convenience, the second filters 74 and diffusers 78 are shown in FIG. 2 as having different sizes, but are not required to be of different sizes to practice the invention. In some configurations, second filters 74 and diffusers 78 have the same size and same geometric shape, but in some configurations, the second filters 74 and diffusers 78 have different sizes and geometric shapes. Each LED 70 is enclosed in one of a plurality of recesses 82 that are covered by second filters 74 and diffusers 78. However, in some configurations, illuminator 38 includes a plurality of any suitable excitation light sources other than LEDs 70, for example, tungsten or xenon bulbs, a laser light source, and/or a fiber optic light source.

The LEDs 70 are configured to emit a wavelength of light at an intensity level that excites a fluorescent marker in each feature. For example, in some configurations, the illuminator 38 includes LEDs 70 that emit light having a wavelength of about 635 nm to excite fluorescent markers that emit red light.

In some configurations, the illuminator 38 includes LEDs 70 that emit light having a wavelength of about 470 nm used to excite fluorescent markers that emit blue light. Other wavelengths may be used to excite fluorescent markers having other excitation requirements. In various configurations the Illuminator 38 includes LEDs 70 that emit light having various wavelengths. For example, various LEDs 70 emit light having a wavelength of 635 nm, while other LEDs 70 in illuminator 38 emit light having a wavelength of 470 nm, and other LEDs 70 may emit light having other wavelengths. This would allow the use of multi-color fluorescent markers in the array of features.

In various configurations, imaging apparatus 10 is configured to allow the illuminator 38 to be removed and replaced with an illuminator 38 comprising LEDs that emit light having a different wavelength. Thus, if tile 42 associated with an array of features having fluorescent markers that emit red light is removed and replaced with a tile 42 associated with an array of features having fluorescent markers that emit blue light, the illuminator 38 can be removed and replaced accordingly.

Furthermore, in some configurations, each of the LEDs 70 is oriented in the recesses 82 so that light provided by each LED 70 is directed toward one or more desired areas of the tile 42. For example, each LED 70 can be oriented so that light emitted from each LED is generally directed to the center of the tile 42, or each LED 70 can be oriented so that light emitted from each LED is directed to different sections of the tile 42. In various configurations, a front face 84 of the illuminator 38 is angled inward to allow the LEDs 70 to point downward and slightly inward toward a focal point in the center of the tile 42.

In some configurations, the diffusers 78 diffuse light emitted from each LED 70 to substantially evenly distribute the light from each LED 70 over the entire tile 42. That is, diffusers 78 have a divergence angle selected so that light emitted from each LED 70 illuminates the entire tile 42. Therefore, the light emitted from each LED 70 overlaps with the light emitted from each of the other LEDs 70. Thus, the intensity of light provided by the illuminator 38, over the entire tile 42 is a function of the number of LEDs included in the illuminator 38 and the selected intensity of the LEDs 70. In some configurations, a single diffuser (not shown) is used. In various configurations the single diffuser has the same shape as the front face 84 of illuminator 38. The single diffuser covers each LED 70 and simultaneously diffuses the light emitted from each LED 70. In various other configurations at least two diffusers (not shown) are used to diffuse light emitted by the LEDs 70.

The second filters 74 eliminate light emitted by the LEDs 70 having a wavelength that would reflect off the array, the tile 42, or the stage 38 and undesirably pass through the first filter 54 to the image collecting device 58. For example, in some configurations, the first filter 54 passes light having a wavelength greater than about 640 nm, and the second filter 74 passes only light having a wavelength of less than about 635 nm. In some configurations, the second filters 74 are short-pass filters adapted to pass light having shorter wavelengths, for example light having a wavelength less than about 635 nm. In some configurations, the second filter 74 is a bandpass filter adapted to pass light having wavelengths included in a certain range of wavelengths, for example light having wavelengths that are between about 550 nm and about 635 nm. In various configurations, the apparatus 10 includes a single second filter (not shown) for eliminating light emitted by the LEDs 70. In various other configurations, the apparatus 10 includes two or more second filters (not shown), whereby each of the second filters 74 filters light emitted by at least one of the LEDs 70.

In various configurations, EPI illumination is utilized, in place of the illuminator 38, to illuminate the array and excite the fluorescent markers. An EPI based system would have a dichroic beam splitter (not shown) between the first lens 46 and the first filter 54. Light emitted from the EPI illuminator would be shaped and imaged onto the sample tile 42 through the first lens 46. LEDs, a lamp or a laser could be used as the illumination source. Any suitable illumination source can be utilized to illuminate the array and excite the fluorescent markers. For example, off axis illumination and electro luminescent panels can be utilized.

Referring to FIG. 1, the first filter 54 is positioned between the first lens 46 and the second lens 50 when it is desirable to filter out light reflecting off the array from the illuminator 38 having certain wavelengths. Therefore, light emitted from the illuminator 38 that overlaps with the fluorescent emissions of the array of features is separated from the fluorescent emissions and substantially prevented from reaching the image collecting device 58. The first filter 54 can be removed when filtering is not desired, for example, when chemiluminescent emissions are to be imaged, all light that can interfere with the enzymatically generated chemiluminescent signals must be substantially removed from the environment surrounding the imaging apparatus 10. In some configurations, the removal and insertion of the first filter 54 is automated by the controller and a mechanism (not shown) suitable for inserting the first filter 54 between the first and second lenses 46 and 50, and removing the first filter 46 when desired.

In some configurations, a filter wheel having a plurality of filters is used as a first filter 54, wherein each filter of the filter wheel filters out light of a different wavelength, or within a different bandwidth. Positioning of the filter wheel is automated by the controller and a mechanism suitable to rotate the wheel such that a desired filter, or no filter, is positioned between the first and second lenses 46 and 50. The first filter 54 works in combination with the second filter 78 to allow only fluorescent emissions of the array to be collected by the image collecting device 58 when the illuminator 38 is illuminated.

Figure 3:
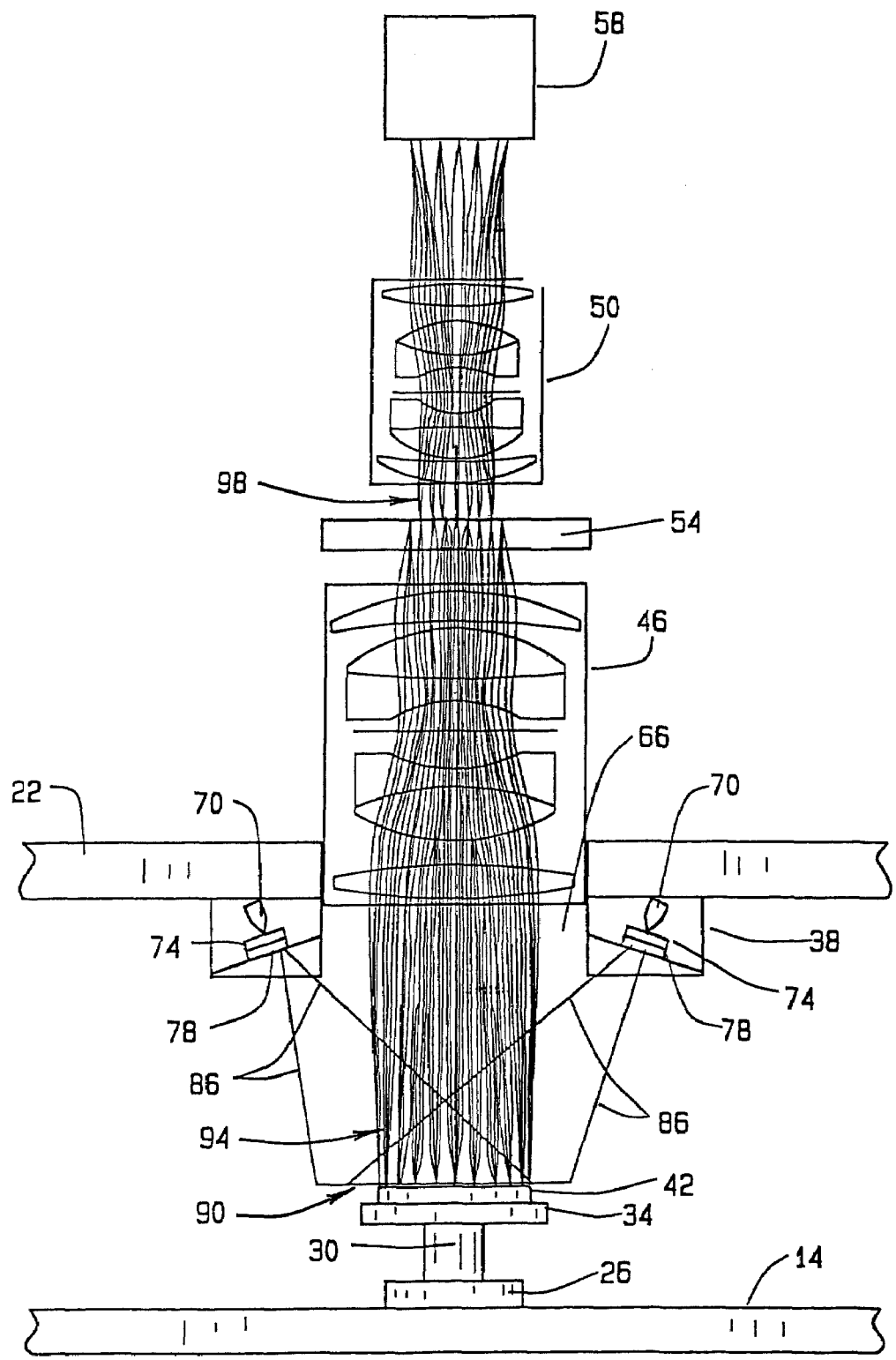
FIG. 3 is a schematic of a cross-section of the imaging apparatus shown in FIG. 1, illustrating illumination patterns of the illuminator shown in FIG. 2.

FIG. 3 is a schematic of a cross-section of various configurations of the imaging apparatus 10 (shown in FIG. 1), illustrating the flood illumination of the illuminator 38 (shown in FIG. 2) and the path of the fluorescent signals emitted from an array of features. Each LED 70 emits light directed at the tile 42 and the associated array. The light emitted by each LED 70 is filtered by the second filter 78 so that only light having a desired wavelength, or within a desired range of wavelengths, illuminates the tile 42 and associated array. Additionally, light emitted from each LED 70 is diffused by the diffuser 78 to provide a substantially uniform intensity of light over the entire tile 42, as indicated by LED illumination pattern lines 86. Therefore, the light emitted from each LED 70 overlaps with the light emitted from at least one of the other LEDs 70, as generally indicated at overlap area 90.

The light emitted by the LEDs 70, filtered by the second filters 74, and diffused by the diffusers 78, excites the fluorescent markers in each feature of the array, resulting in the emission of fluorescent signals 94. The fluorescent signals 94 pass through the opening 66 in the illuminator 38 and enter the first lens 46, where they are re-imaged. The signals 94 are then filtered by the first filter 54, which filters out any light from the LEDs 70 that has reflected off of the array of features, the tile 42 and/or the stage 34. The filtered signals 98 then pass through the second lens 50 where they are re-imaged again. After passing through the second lens 50, the fluorescent signals 94 are collected by image collecting device 58, and the collected image data is transmitted to a computer based system (not shown), where the data is processed and analyzed.

Figure 4:
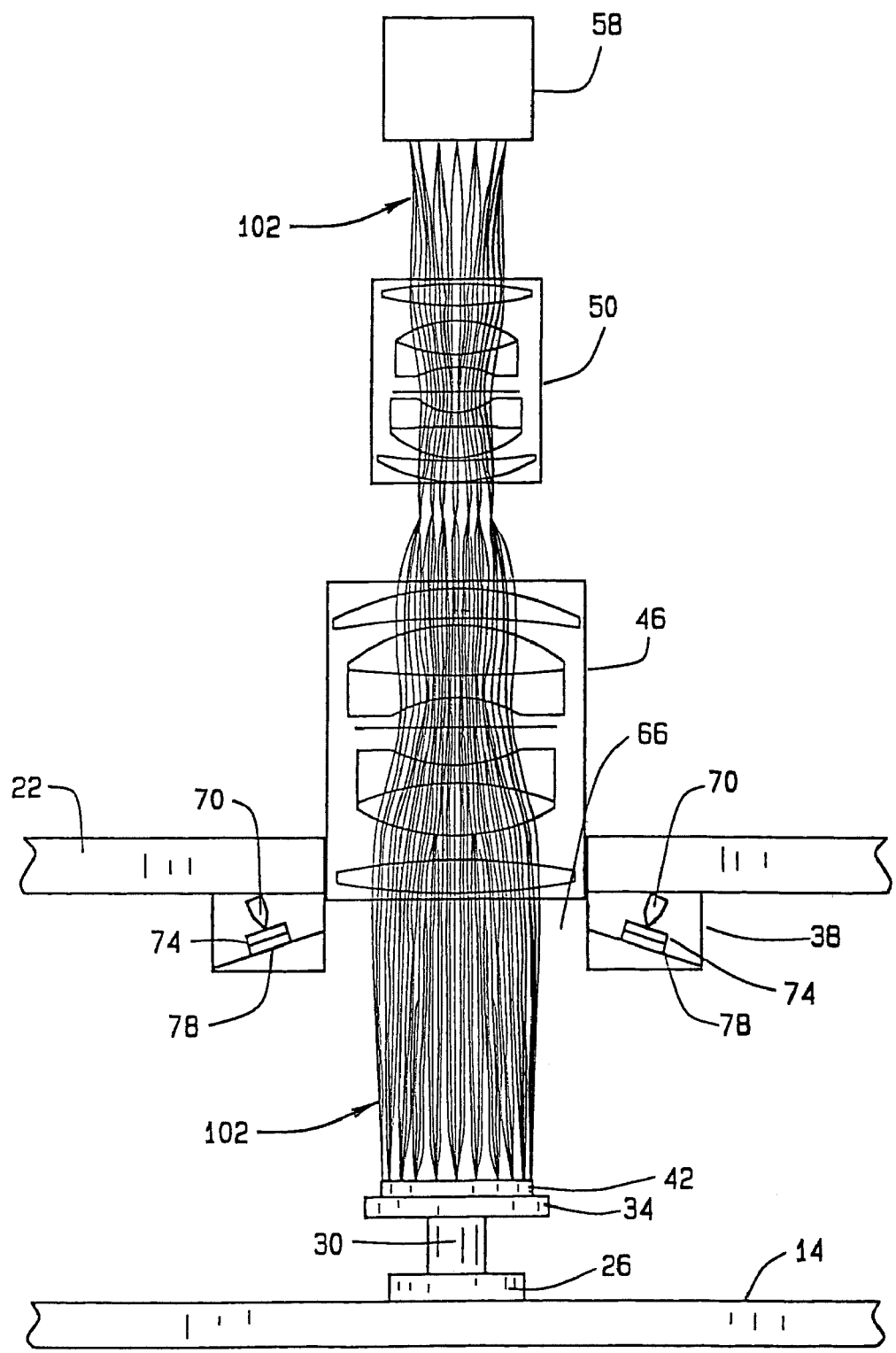
FIG. 4 is a schematic of a cross-section of the imaging apparatus shown in FIG. 1, illustrating the path of the chemiluminescent signals emitted from an array of features.

FIG. 4 is a schematic of a cross-section representative of various configurations of imaging apparatus 10 (shown in FIG. 1), illustrating the path of the chemiluminescent signals emitted from an array of features. To collect images of chemiluminescent signals 102 emitted by the feature in the array, the first filter 54 (shown in FIG. 3) is removed from between the first and second lenses 46 and 50, and the illuminator 38 is turned off. The chemiluminescent signals must be imaged in a substantially light free environment. That is, an environment substantially free from any light that will interfere with the chemiluminescent signals emitted from the array.

In various configurations the chemiluminescent signals are enzymatically generated. Methods for generating chemiluminescent signal in biomolecular array, for example nucleic acid microarrays, have been described in U.S. Pat. Nos. 5,625,077, 5,652,345, 5,679,803, 5,783,381, 6,022,964, 6,133,459, and 6,124,478.

The chemiluminescent signals 102 emitted from the array pass through the first and second lenses 46 and 50, where the chemiluminescent signals 102 are re-imaged by each lenses 46 and 50. After passing through the lenses 46 and 50, the chemiluminescent signals 102 are collected by image collecting device 58. The collected image data is then transmitted to the computer based system, where the data is processed and analyzed. In various configurations, each feature may have more than one chemiluminescent marker hybridized with probes associated with the tile 42. In which case, the first filter 54 would not be removed in order to filter out light emitted from one of the chemiluminescent markers of the features while allowing wavelengths of different chemiluminescent signals to pass and be imaged by the image collecting device 58. The first filter 54 would then be removed and replaced with a different first filter 54 that would allow other chemiluminescent signals to be imaged.

Referring now to both FIGS. 3 and 4, in various configurations, the filtered fluorescent signals 98 collected by image collecting device 58 are used to auto-focus the array of features for the image collecting device 58, as described above in reference to FIG. 1, for example corrections for chromatic aberrations are made. Additionally, the filtered fluorescent signals 98 collected by image collecting device 58 are used for gridding the array of features. That is, the filtered fluorescent signals 98 are used to identify the location of each feature within the array. Furthermore, the filtered fluorescent signals 98 collected by image collecting device 58 are used to normalize the array. More specifically, the filtered fluorescent signals 98 are used to normalize the chemiluminescent signals 102 collected by the image collecting device 58.

Figure 5:
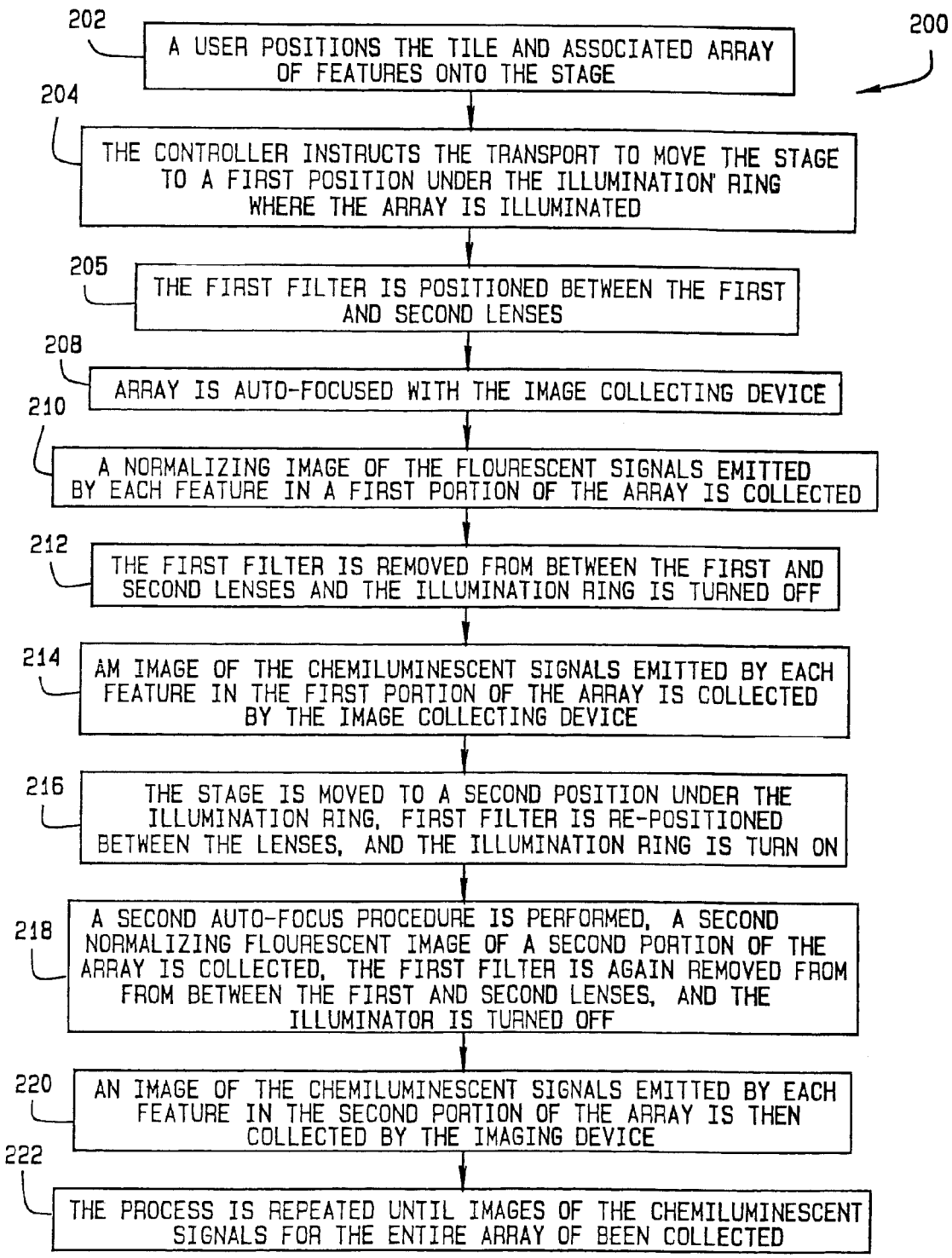
FIG. 5 is a flow chart for the basic operation of the imaging apparatus shown in FIG. 1.

FIG. 5 is a flow chart 200 representative of various method configurations for operating an imaging apparatus 10 for imaging an array of features. To begin, a user positions the tile 42 and associated array of features onto the stage 34, as indicated at 202. The controller instructs the transport 26 to move the stage 34 along the x-axis to a first position under the illuminator 38, where the array is illuminated by the illuminator 38, as indicated at 204. Next the first filter 54 is positioned between the first and second lenses 46 and 50, as indicated at 206. The array is then auto-focused for the image collecting device 58 by moving the stage 34 along the z-axis, via the elevator 30, as indicated at 208. A normalizing image of the fluorescent signals 98 emitted by each feature in a first portion of the array is then collected, as indicated at 210.

Next, the first filter 54 is removed from between the first and second lenses 46 and 50, and the illuminator 38 is turned off, as indicated at 212, thereby providing a substantially light free environment for imaging the chemiluminescent signals emitted by each feature. Then an image of the chemiluminescent signals 102 emitted by each feature in the first portion of the array is collected by the image collecting device 58, as indicated at 214.

Next, in various configurations, depending on the size of the array, the stage 30 is moved to a second position under the illuminator 38, first filter 54 is re-positioned between the lenses 46 and 50, and the illuminator 38 is turned on, as indicated at 216. Then, a second auto-focus procedure is performed, a normalizing fluorescent image of a second portion of the array is collected, the first filter 54 is again removed from between the first and second lenses 46 and 50, and illuminator 38 is again turned off, as indicated at 218. An image of the chemiluminescent signals 102 emitted by each feature in the second portion of the array is then collected by the imaging device 58, as indicated at 220. This process is repeated, as needed, until images of the chemiluminescent signals 102 for the entire array have been collected, as indicated at 222.

Thus, the imaging apparatus of the present invention automatically acquires multiple images of an array of fluorescent/chemiluminescent co-hybridized features, thereby acquiring image data for the entire array using a single apparatus. Additionally, the present invention allows better alignment between the fluorescent and the chemiluminescent image data because the optics are the same for the collection in both channels. Furthermore, the illuminator substantially evenly distributes excitation light over the entire array, thereby providing more consistent image data for multiple images across the entire array.

While the invention has been described in terms of various configurations, those skilled in the art will recognize that the invention can be practiced with modification within the spirit and scope of the claims.

What is claimed is:

1. A method for collecting images of signals using an imaging apparatus, the method comprising:
   placing a sample tile on a stage of the imaging apparatus, the sample tile having an array including a plurality of features, at least a portion of the features each having a hybridized sample;
   introducing a first excitation energy upon an area of the sample tile, flooding an entirety of the area of the sample tile with the first excitation energy, and causing a first signal to be emitted;
   collecting a first image of at least a portion of the array utilizing an image collecting device of the imaging apparatus, the first image being representative of the first signal; and
   collecting a second image of at least a portion of the array utilizing the image collecting device of the imaging apparatus, the second image being representative of a second signal, the second signal being different than the first signal.

2. The method according to claim 1 wherein the introducing a first excitation energy upon the area of the sample tile comprises introducing the first excitation energy from a laser source upon the area of the sample tile.

3. The method according to claim 1, further comprising:
   moving the stage from a first position to a second position, the second position being generally under the image collecting device.

4. The method according to claim 1, further comprising:
moving the stage from a first position to a second position along an x-axis, the second position being generally under the image collecting device.

5. The method according to claim 1, further comprising:
moving the stage from a first position to a second position, the second position being generally at a focal plane of the image collecting device.

6. The method according to claim 1, wherein the introducing the first excitation energy upon the area of the sample tile causing the first signal to be emitted comprises introducing the first excitation energy upon the area of the sample tile causing a fluorescent signal to be emitted.

7. The method according to claim 1 wherein the second signal comprises a chemiluminescent signal.

8. The method according to claim 1, further comprising:
positioning a filter between the stage and the image collecting device of the imaging apparatus, the filter filtering at least a portion of one of the first signal and the second signal.

9. An imaging system for collecting images of signals associated with a sample tile, the imaging system comprising:
a stage supporting the sample tile;
an illuminator system emitting excitation energy upon the sample tile causing at least a first signal to be generated from the sample tile, wherein the illuminator system comprises a diffuser diffusing the excitation energy such that the sample tile is flooded with the excitation energy from a plurality of directions; and
an image collecting device collecting a first image of the first signal, the image collecting device further collecting a second image of a second signal emitted from the sample tile, the second signal being different than the first signal.

10. The imaging system according to claim 9 wherein the stage is movable from a first position to a second position, the second position being generally under the image collecting device.

11. The imaging system according to claim 9 wherein the illuminator system comprises a plurality of sources outputting the excitation energy such that the sample tile is flooded with the excitation energy from a plurality of directions.

12. The imaging system according to claim 9 wherein the illuminator system floods an entirety of the sample tile with the excitation energy.

13. The imaging system according to claim 9 wherein the illuminator system comprises a laser.

14. The imaging system according to claim 9 wherein the illuminator system is positioned between the image collecting device and the stage.

15. The imaging system according to claim 9 wherein the illuminator system comprises a filter filtering the excitation energy emitted by the illuminator system.

16. The imaging system according to claim 9 wherein the image collecting device is a charge-coupled device (CCD).

17. The imaging system according to claim 9 wherein the first signal is a fluorescent signal and the second signal is a chemiluminescent signal.

18. The imaging system according to claim 9 wherein the image collecting device collects the second image in the absence of the first excitation energy.

19. The imaging system according to claim 9 wherein the illuminator system outputs two or more wavelengths of the first excitation energy.

20. A method for collecting images of signals using an imaging apparatus, the method comprising:
placing a sample tile on a stage of the imaging apparatus, the sample tile having an array including a plurality of features, at least a portion of the features each having a hybridized sample;
introducing a first excitation energy upon an area of the sample tile causing a first signal to be emitted, comprising flooding an entirety of the sample tile with the first excitation energy;
collecting a first image of at least a portion of the array utilizing an image collecting device of the imaging apparatus, the first image being representative of the first signal;
introducing a second excitation energy upon the area of the sample tile causing a second signal to be emitted, the second excitation energy being a different wavelength than the first excitation energy, the second signal being different than the first signal; and
collecting a second image of at least a portion of the array utilizing the image collecting device of the imaging apparatus, the second image being representative of the second signal.

21. The method according to claim 20, further comprising:
positioning a filter between the stage and the image collecting device of the imaging apparatus.

* * * * *